United States Patent
Knott et al.

(10) Patent No.: US 11,026,833 B2
(45) Date of Patent: Jun. 8, 2021

(54) TEMPERATURE CONTROL DEVICE FOR FLUID-BASED HYPER/HYPOTHERMIA SYSTEMS

(71) Applicant: Sorin Group Deutschland GmbH, Munich (DE)

(72) Inventors: Erwin Knott, Poing (DE); Manfred Fronhöfer, Munich (DE)

(73) Assignee: LivaNova Deutschland GmbH, München (DE)

( * ) Notice: Subject to any disclaimer, the term of this patent is extended or adjusted under 35 U.S.C. 154(b) by 437 days.

(21) Appl. No.: 15/703,292

(22) Filed: Sep. 13, 2017

(65) Prior Publication Data
US 2018/0000634 A1 Jan. 4, 2018

Related U.S. Application Data

(63) Continuation of application No. 14/147,764, filed on Jan. 6, 2014, now abandoned, which is a continuation
(Continued)

(30) Foreign Application Priority Data

Apr. 8, 2011 (DE) .......................... 102011016508.8

(51) Int. Cl.
*A61F 7/00* (2006.01)
*A61M 1/36* (2006.01)

(52) U.S. Cl.
CPC ........... *A61F 7/0085* (2013.01); *A61M 1/369* (2013.01); *A61M 2205/3368* (2013.01);
(Continued)

(58) Field of Classification Search
CPC .......... A61M 1/369; A61M 2205/0056; A61M 2205/16; A61M 2205/36;
(Continued)

(56) References Cited

U.S. PATENT DOCUMENTS

| 3,064,649 A | 11/1962 | Fuson |
| 3,614,534 A | 10/1971 | Gross |

(Continued)

FOREIGN PATENT DOCUMENTS

| AU | 07682/51 B2 | 12/2003 |
| AU | 768251 B2 | 12/2003 |

(Continued)

OTHER PUBLICATIONS

International Preliminary Report on Patentability issued in PCT/EP2012/056154, completed Aug. 13, 2013, 10 pages.
(Continued)

*Primary Examiner* — Daniel W Fowler
(74) *Attorney, Agent, or Firm* — Seager, Tufte & Wickhem LLP.

(57) ABSTRACT

Temperature control device for use in fluid-based hyper/hypothermia systems, comprising a connection unit for connecting the device to a local power network, and a fluid temperature control unit for heating or cooling a fluid. The device includes a power supply unit, by which electrical consuming components of the fluid temperature control unit are supplied with power, and which effects supply of the electrical consuming components with direct current.

12 Claims, 2 Drawing Sheets

Related U.S. Application Data of application No. 13/441,603, filed on Apr. 6, 2012, now Pat. No. 9,351,869.

(52) U.S. Cl.
CPC ..... *A61M 2205/36* (2013.01); *A61M 2205/82* (2013.01); *A61M 2205/8206* (2013.01); *F04C 2270/041* (2013.01)

(58) Field of Classification Search
CPC .. A61M 2205/3331; A61M 2205/3368; A61M 2205/3606; A61M 2205/82; A61M 2205/8602; A61B 18/02; A61B 2018/00744; A61B 2018/00714; A61B 2018/00791; A61B 2018/046; A61B 2018/048
See application file for complete search history.

(56) References Cited

U.S. PATENT DOCUMENTS

| | | | |
|---|---|---|---|
| 4,180,896 A | 1/1980 | Cooley et al. |
| 4,221,543 A | 9/1980 | Cosentino et al. |
| 4,231,425 A | 11/1980 | Engstrom |
| 4,298,006 A | 11/1981 | Parks |
| 4,517,633 A | 5/1985 | Melcher |
| 4,966,145 A | 10/1990 | Kikumoto et al. |
| 5,019,076 A | 5/1991 | Yamanashi et al. |
| 5,117,834 A | 6/1992 | Kroll et al. |
| 5,242,404 A | 9/1993 | Conley et al. |
| 5,247,434 A | 9/1993 | Peterson et al. |
| 5,409,612 A | 4/1995 | Maltais et al. |
| 5,487,827 A | 1/1996 | Peterson et al. |
| 5,647,984 A | 7/1997 | Hovland et al. |
| 5,730,720 A | 3/1998 | Sites et al. |
| 5,863,501 A | 1/1999 | Cosentino |
| 5,871,526 A | 2/1999 | Gibbs et al. |
| 5,900,256 A | 5/1999 | Scoville, Jr. et al. |
| 6,117,164 A | 9/2000 | Gildersleeve et al. |
| 6,156,007 A | 12/2000 | Ash |
| 6,175,668 B1 | 1/2001 | Cassidy et al. |
| 6,581,403 B2 | 6/2003 | Whitebook et al. |
| 6,635,076 B1 | 10/2003 | Ginsburg |
| 6,655,394 B1 | 12/2003 | Tanaka et al. |
| 6,891,136 B2 | 5/2005 | Bikovsky et al. |
| 6,939,347 B2 | 9/2005 | Thompson |
| 6,981,794 B2 | 1/2006 | Bibbo et al. |
| 7,094,231 B1 | 8/2006 | Ellman et al. |
| 7,176,419 B2 | 2/2007 | Ellis et al. |
| 7,220,260 B2 | 5/2007 | Fleming et al. |
| 7,900,629 B2 | 3/2011 | Gurnee et al. |
| 8,231,664 B2 | 7/2012 | Kulstad et al. |
| 8,308,787 B2 | 11/2012 | Kreck |
| 8,343,202 B2 | 1/2013 | Magers |
| 8,475,509 B2 | 7/2013 | Dae |
| 9,259,523 B2 | 2/2016 | Schreyer et al. |
| 9,351,869 B2 | 5/2016 | Knott et al. |
| 9,927,416 B2 | 3/2018 | Schreyer et al. |
| 9,956,308 B2 | 5/2018 | Schreyer et al. |
| 2003/0060864 A1 | 3/2003 | Whitebook et al. |
| 2004/0068310 A1 | 4/2004 | Edelman |
| 2004/0149711 A1 | 8/2004 | Wyatt et al. |
| 2004/0267340 A1 | 12/2004 | Cioanta et al. |
| 2005/0047959 A1 | 3/2005 | Brandl et al. |
| 2005/0284815 A1 | 12/2005 | Sparks et al. |
| 2007/0020142 A1 | 1/2007 | Federspiel et al. |
| 2009/0012450 A1 | 1/2009 | Shah et al. |
| 2009/0056344 A1 | 3/2009 | Poch |
| 2009/0069731 A1 | 3/2009 | Parish et al. |
| 2010/0030306 A1 | 2/2010 | Edelman et al. |
| 2010/0106229 A1 | 4/2010 | Gammons et al. |
| 2010/0143192 A1 | 6/2010 | Myrick et al. |
| 2011/0107251 A1 | 5/2011 | Guaitoli et al. |
| 2012/0167879 A1 | 7/2012 | Bowman et al. |
| 2012/0259394 A1 | 10/2012 | Knott et al. |
| 2012/0308431 A1 | 12/2012 | Kotsos et al. |
| 2013/0079763 A1 | 3/2013 | Heckel et al. |
| 2013/0116761 A1 | 5/2013 | Kreck |
| 2013/0280692 A1 | 10/2013 | Gourlay |
| 2013/0324619 A1 | 12/2013 | Chtourou |
| 2013/0331739 A1 | 12/2013 | Gertner |
| 2014/0014580 A1 | 1/2014 | Ritter |
| 2014/0121734 A1 | 5/2014 | Knott et al. |
| 2014/0308654 A1 | 10/2014 | Kay et al. |
| 2015/0217014 A1 | 8/2015 | Schreyer et al. |
| 2015/0265759 A1 | 9/2015 | Schreyer et al. |
| 2016/0139100 A1 | 5/2016 | Schreyer et al. |
| 2017/0216509 A1 | 8/2017 | Bellini |
| 2017/0267907 A1 | 9/2017 | Knott et al. |
| 2018/0243455 A1 | 8/2018 | Schreyer et al. |

FOREIGN PATENT DOCUMENTS

| | | |
|---|---|---|
| CN | 1202116 A | 12/1998 |
| CN | 201871012 U | 6/2011 |
| CN | 202154894 U | 3/2012 |
| CN | 102526822 A | 7/2012 |
| DE | 3883452 T2 | 8/1993 |
| DE | 19531935 A1 | 2/1997 |
| DE | 19924856 A1 | 12/2000 |
| DE | 69331840 T2 | 4/2002 |
| DE | 69634572 T2 | 2/2006 |
| EP | 0297723 A2 | 1/1989 |
| EP | 1267958 A2 | 1/2003 |
| EP | 1970080 A1 | 9/2008 |
| EP | 2698176 A1 | 2/2014 |
| EP | 2698177 B1 | 1/2015 |
| FR | 2631241 A1 | 11/1989 |
| JP | 54-154195 A | 12/1979 |
| JP | 61-131753 A | 6/1986 |
| JP | 11-057733 A | 3/1999 |
| JP | 2001-506971 A | 5/2001 |
| JP | 2002-539893 A | 11/2002 |
| JP | 2003-260131 A | 9/2003 |
| JP | 2005-074236 A | 3/2005 |
| JP | 2005514085 A | 5/2005 |
| JP | 2005-219041 A | 8/2005 |
| JP | 2008-111612 A | 5/2008 |
| JP | 2014-503305 A | 2/2014 |
| WO | 97/06840 A1 | 2/1997 |
| WO | WO2001072352 A2 | 10/2001 |
| WO | 03/54660 A2 | 7/2003 |
| WO | WO2006063080 A1 | 6/2006 |
| WO | 2009/094601 A2 | 7/2009 |
| WO | 2014/026833 A1 | 2/2014 |

OTHER PUBLICATIONS

International Search Report and Written Opinion issued in PCT/EP2012/056154, dated Jun. 26, 2012, 9 pages.
Netzteil (English: Power Supply), downloaded from German Wikipedia on Apr. 5, 2011, with English Wikipedia translation downloaded on Dec. 23, 2013.
Schaltnetzteil (English: Switching Power Supply), downloaded from German Wikipedia on Mar. 30, 2011, with English Wikipedia translation downloaded on Dec. 23, 2013, 13 pages.
Extended European Search Report issued in EP application 1615495.3, dated Feb. 14, 2017, 9 pages.

TEMPERATURE CONTROL DEVICE FOR FLUID-BASED HYPER/HYPOTHERMIA SYSTEMS

CROSS-REFERENCE TO RELATED APPLICATION

This application is a continuation of U.S. application Ser. No. 14/147,764, filed Jan. 6, 2014, which is a continuation of U.S. application Ser. No. 13/441,603, filed Apr. 6, 2012, now U.S. Pat. No. 9,351,869, which claims priority to German Application No. 10 2011 016 508.8, filed Apr. 8, 2011, which are herein incorporated by reference in their entirety.

TECHNICAL FIELD

The invention relates to a temperature control device for use in fluid-based hyper/hypothermia systems.

BACKGROUND

A fluid-based hyper/hypothermia system is disclosed, for example, in DE 696 34 572 T2. Fluid-based hyper/hypothermia systems that use a temperature-controlled fluid to raise the temperature of a human or animal body, body part or organ to above the normal core body temperature or to lower it to below the normal core body temperature require a temperature control device that provides a temperature-controlled fluid to accomplish the desired change in body temperature. The temperature of the fluid must be controlled in the temperature control device in accordance with the quantity of heat to be supplied to or removed from the body. The fluid, for example, must be heated or cooled and then maintained at a predetermined temperature.

SUMMARY

In order to heat or cool the fluid in a temperature control device, energy is required that is provided as a general rule by the local power network. Thus, a conventional temperature control device comprises a power supply which allows the temperature control device to be connected to the local power network. Both the power supply as well as numerous individual electrical consuming components of the temperature control device must be adapted to the local power network. Since there are different local power networks in different regions of the world, the region of the world in which the temperature control device is ultimately supposed to be used and the specifications of the local power network according to which the power supply of the temperature control device and the temperature control device itself have to be configured must, with a considerable amount of effort, always be taken into consideration when constructing a temperature control device for hyper/hypothermia applications.

Various embodiments of the invention simplify the construction of a temperature control device and provide a temperature control device for hyper/hypothermia systems that can be used in different regions of the world. This aim is achieved by a temperature control device for use in fluid-based hyper/hypothermia systems, comprising: a connection unit for connecting the device to a local power network; and a fluid temperature control unit for heating or cooling a fluid including a power supply unit that supplies electrical consuming components of the fluid temperature control unit with power, and supplies the electrical consuming components with direct current.

DETAILED DESCRIPTION

Figure 1:
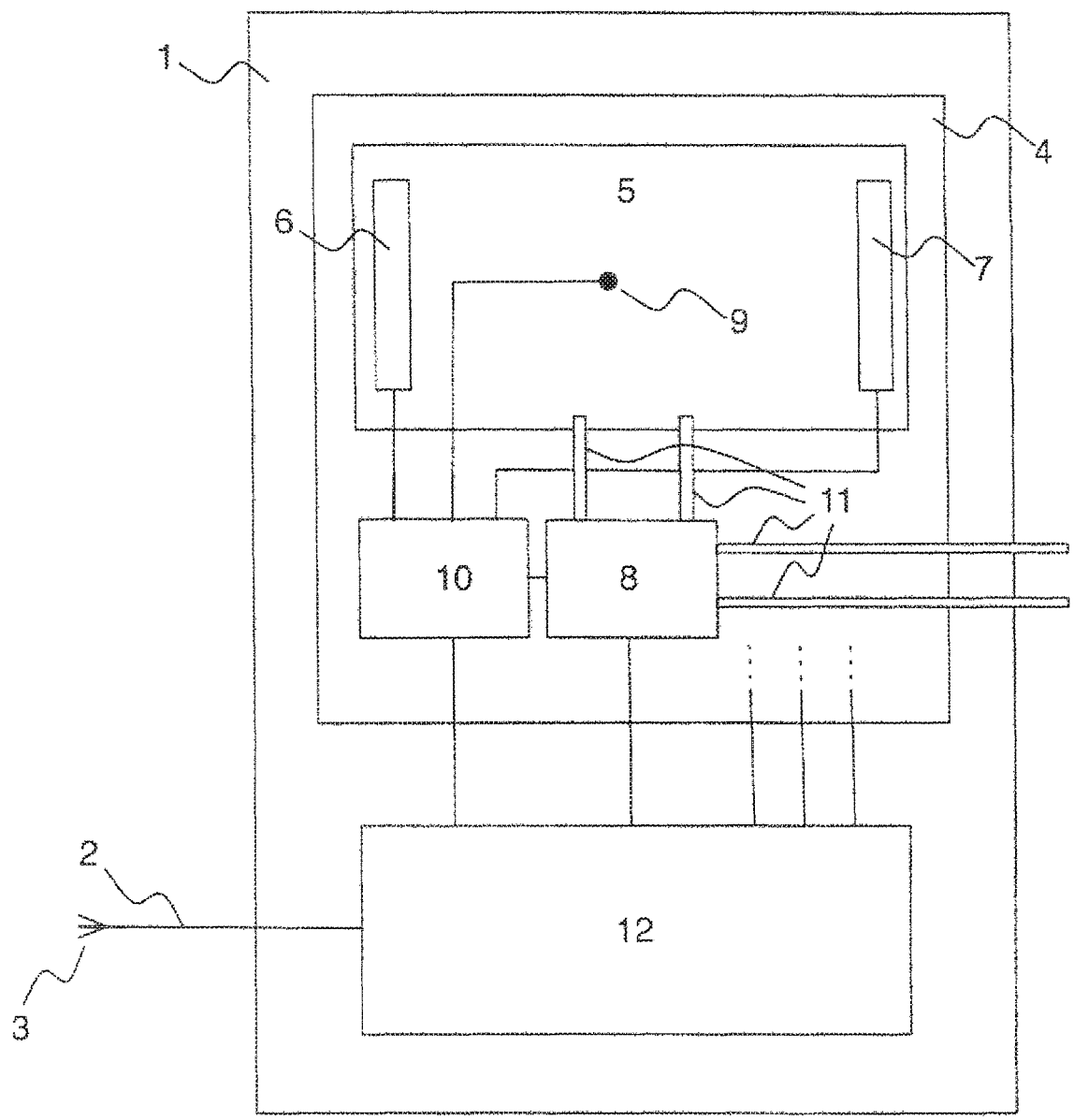
FIG. 1 shows an embodiment of a temperature control device according to the invention.

FIG. 1 shows a temperature control device 1 for use in a fluid-based hyperthermia or hypothermia system, according to embodiments of the invention. As shown in FIG. 1, the control device 1 includes a connection unit 2 for connecting the device to a local power network 3. In Germany, for example, the local power network is a general alternating current (AC) network of 220/380 V at 50 Hz. In Japan, for example, the local power network is an AC network of 100 V at, for example, 60 Hz. And in the United States, for example, the local power network is an AC network of 120 V at 60 Hz. These differences, and in particular the differences in frequency of the local power networks, lead to differences in the leakage currents which result from the change of the connected alternating current over time. For medical-technical systems in a surgical environment, the effects of electrical leakage currents, in the case for example of open heart surgeries, must remain minimal. To minimize these leakage currents, the electric lines in conventional temperature control devices must have certain insulations. This leads to increased material costs since, in particular, the insulation can age and must then be replaced if the guidelines with respect to the leakage currents are no longer met.

The temperature control device, according to the illustrative embodiments of the invention, is connected to the power network 3 via the connection unit 2 and can draw the power required to control the temperature of the fluid from the power network.

The temperature control of the fluid is accomplished by means of a fluid temperature control unit 4 which includes the components required for heating or cooling the fluid. These normally include a fluid container 5, a heater 6, a cooler 7, a supply pump 8, a temperature sensor 9 and a temperature controller 10 (e.g., a microprocessor), each of which are shown in FIG. 1 merely in schematic form and as an example of the components of the fluid temperature control unit 4. In this embodiment, the supply pump 8 works, for example, with a direct current motor and the cooler 7 includes a direct current compressor. Also shown by way of an example are pipelines 11, via which the pump 8 removes the fluid from the fluid container 5 and conveys it to the outside such that it can be used in the hyper/hypothermia system, or via which the fluid is conveyed out of the hyper/hypothermia system back into the fluid container 5. The pump can also be provided in the hyper/hypothermia system such that it can be omitted from the fluid temperature control unit 4 of a temperature control device 1 as according to the invention. Depending on the hyper/hypothermia system in which the temperature control device 1 is used, other components, such as a stirrer for the fluid in the fluid container 5, may be added to (or omitted from) the fluid temperature control unit 4. According to various embodiments, each of the components shown in FIG. 1 may be of the type disclosed in DE 696 34 572 T2, which is hereby incorporated by reference in its entirety.

To supply power to the electrical consuming components, for example, the heater 6, the cooler 7, the supply pump 8 and the temperature controller 10, of the fluid temperature control unit of a temperature control device 1, a power supply unit 12 is provided according to the invention, via which all of the electrical consuming components of the fluid temperature control unit 4 are electrically supplied with constant connected loads irrespective of the local power network. According to embodiments of the invention, direct current is supplied, for example, with a supply voltage of 48 V and a power of up to 3.5 kW. Accordingly, the electrical consuming components of the fluid temperature control unit 4 are supplied via the power supply unit and are, thus, not directly connected to the power network 3. Thus, these components need not be designed for the local power network, but are instead all supplied with direct current by the power supply unit 12. Different electrical consuming components can thereby be supplied with different voltages/powers which are provided by the power supply unit 12 according to the invention. This is indicated in FIG. 1 by the connections between the power supply unit 12 and the fluid temperature control unit 4, which are dashed at one end. The power supply unit 12 thereby performs adaptation to the local power network and conversion to a power supply with constant connected loads.

The power supply unit thus performs any and all necessary conversions to adapt the temperature control device to the conditions of a local or regional power network. The adaptation to the local power network of the region in which the device is to be used is achieved by an appropriate design of the power supply unit, which, on the side facing the connection unit, must be designed for connection to the local power network, but on the side facing the fluid temperature control unit, a uniform power supply with direct current is ensured irrespective of the local power network.

The power supply unit may be any standard power supply (including, for example, switched-mode power supplies) that provides (as standard) one or more of the supply voltages required by the fluid temperature control unit, so that the temperature of the fluid can be controlled. In this way, the fluid temperature control unit is electrically separate from the local power network. As a result, an improved electrical decoupling of the fluid temperature control unit from the power network is achieved, which has a positive effect on use in hyper/hypothermia systems, since network feedback and leakage currents can be reduced. In view of the fact that medical-technical systems such as hyper/hypothermia systems are subject to particularly critical specifications, this decoupling of the fluid temperature control unit from the local power network that is achieved by the power supply unit is advantageous.

Supplying the electrical consuming components of the fluid temperature control unit with direct current enables more precise control during operation, since a precise power control for each individual electrical consuming component can take place, for example, with the aid of inverters. This is true not only for the heater/cooler of the fluid temperature control unit, but also for the pumps which are generally electromotively driven. Overall, the improved controllability of the temperature control device of the invention leads to a reduction of noise in a hyper/hypothermia treatment scenario.

Figure 2:
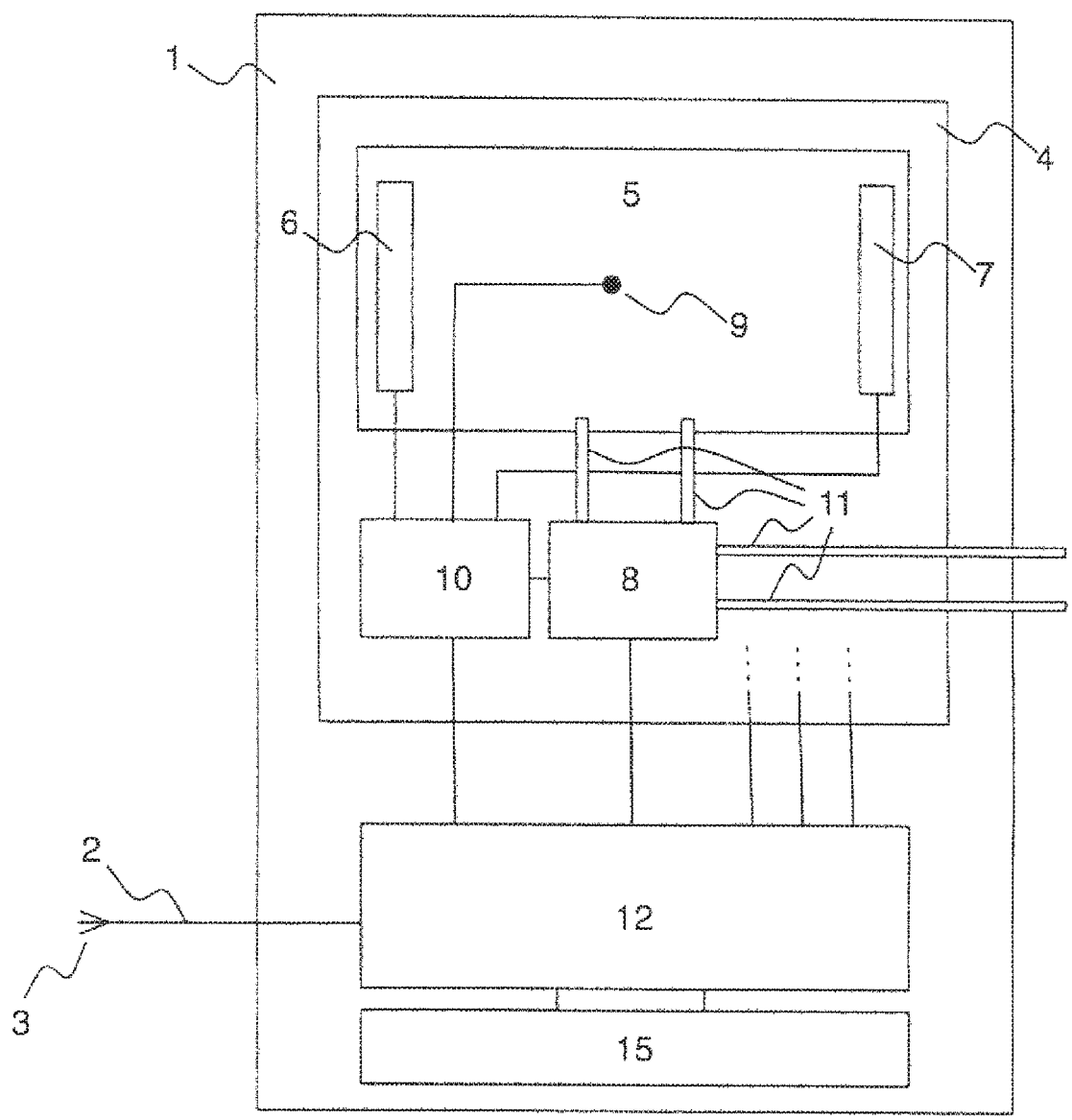
FIG. 2 shows a further embodiment of the temperature control device according to the invention.

FIG. 2 shows further embodiments of a temperature control device 1 according to the invention. As shown in FIG. 2, the control device 1 additionally includes a battery 15 for supplying the electrical consuming components of the fluid temperature control unit 4 with power. The battery 15 is connected to the power supply unit 12 and is charged by this unit when the supply of power occurs via the power network. In this way, the battery 15 can supply power to the power supply unit 12 to ensure delivery of a fail-safe supply of direct current to the electrical consuming components even where the local power network is subject to fluctuations or failure. Thus, designing the temperature control device with direct current electrical consuming components makes it possible to ensure the continuous operation of the temperature control device in a surgical environment.

We claim:

1. A method of running a perfusion hyper/hypothermia system including a temperature control device and a connection unit, wherein the temperature control device includes a fluid temperature control unit including a plurality of electrical consuming components, a supply pump to pump fluid, and a power supply unit, wherein the method of running the perfusion hyper/hypothermia system comprises:
   receiving an alternating current power input from a local power network through the connection unit;
   performing power conversions, using the power supply unit, from the alternating current power input to a plurality of direct current power outputs, such that each of the plurality of direct current power outputs is one of a constant mode output and a variable mode output and the plurality of direct current power outputs includes a first direct current power output that is a first variable mode output and a second direct current power output that is a second variable mode output;
   supplying the plurality of direct current power outputs to the supply pump and the plurality of electrical consuming components including a heater, a cooler, a temperature sensor, and a temperature controller, including supplying the first direct current power output with the first variable mode output to the supply pump and the second direct current power output with the second variable mode output to at least one of the heater and the cooler;
   controlling the plurality of direct current power outputs to regulate a fluid temperature and a pumping rate; and
   circulating the fluid from a fluid container through a pipeline to outside of the temperature control device in the perfusion hyper/hypothermia system and back to the fluid container using the supply pump.

2. The method of claim 1, wherein the alternating current power input is one of 220/380 V at 50 Hz and 100 V to 120 V at 60 Hz.

3. The method of claim 1, wherein the supply pump used to circulate the fluid includes a direct current motor.

4. The method of claim 1, wherein the cooler used to regulate the temperature of the fluid includes a direct current compressor.

5. The method of claim 1, further comprising charging a battery with the power supply unit.

6. The method of claim 1, wherein the power supply unit includes a switched-mode power supply unit.

7. The method of claim 1, wherein the temperature controller includes a microprocessor.

8. A method of running a perfusion hyper/hypothermia system including a temperature control device and a connection unit, wherein the temperature control device includes a supply pump to pump a fluid, a power supply unit, and a fluid temperature control unit including a plurality of electrical consuming components, wherein the method of running the perfusion hyper/hypothermia system comprises:
   receiving an alternating current power input from a local power network through the connection unit;

reducing electrical noise by electrically decoupling the temperature control device from the local power network to reduce network feedback and leakage currents including:

converting the alternating current power input to a plurality of direct current power outputs using the power supply unit, each of the plurality of direct current power outputs being one of a constant mode output and a variable mode output, wherein the plurality of direct current power outputs includes a first direct current power output that is a variable mode output and a second direct current power output that is a constant mode output; and supplying the plurality of direct current power outputs from the power supply unit to the supply pump and the plurality of electrical consuming components including a heater, a cooler, a temperature sensor, and a temperature controller such that each of the supply pump and the plurality of electrical consuming components is supplied with one of the plurality of direct current power outputs and including supplying the first direct current power output with the variable mode output to the supply pump and the second direct current power output with the constant mode output to at least one of the heater and the cooler;

controlling the plurality of direct current power outputs to regulate a temperature and a pumping rate of the fluid; and circulating the fluid from a fluid container through a pipeline to outside of the temperature control device in the perfusion hyper/hypothermia system and back to the fluid container using the supply pump.

9. The method of claim 8, wherein the alternating current power input is one of 220/380 V at 50 Hz, 100 V to 120 V at 60 Hz.

10. The method of claim 8, wherein the supply pump used to circulate the fluid includes a direct current motor.

11. The method of claim 8, wherein the power supply unit includes a switched-mode power supply unit.

12. The method of claim 8, wherein the temperature controller is a microprocessor.

\* \* \* \* \*